United States Patent
Shimomura

(10) Patent No.: US 11,950,759 B2
(45) Date of Patent: Apr. 9, 2024

(54) ENDOSCOPE SYSTEM, CONTROL METHOD, AND CONTROL PROGRAM

(71) Applicant: FUJIFILM Corporation, Tokyo (JP)

(72) Inventor: Koji Shimomura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 87 days.

(21) Appl. No.: 17/819,837

(22) Filed: Aug. 15, 2022

(65) Prior Publication Data

US 2022/0386848 A1    Dec. 8, 2022

Related U.S. Application Data

(63) Continuation of application No. PCT/JP2021/001025, filed on Jan. 14, 2021.

(30) Foreign Application Priority Data

Mar. 24, 2020  (JP) ................. 2020-053412

(51) Int. Cl.
*A61B 1/00* (2006.01)
*A61B 1/06* (2006.01)

(52) U.S. Cl.
CPC ........ *A61B 1/00009* (2013.01); *A61B 1/0005* (2013.01); *A61B 1/06* (2013.01); *A61B 1/00165* (2013.01)

(58) Field of Classification Search
CPC .............. A61B 1/0005; A61B 1/00009; A61B 1/000095; A61B 1/0655; A61B 1/00165; A61B 1/06
USPC ............................................. 348/65; 382/128
See application file for complete search history.

(56) References Cited

U.S. PATENT DOCUMENTS

| 6,636,254 B1 | 10/2003 | Onishi et al. |
| 2012/0086790 A1 | 4/2012 | Takahira et al. |
| 2012/0088969 A1 | 4/2012 | Takahira et al. |
| 2012/0201433 A1 | 8/2012 | Iwasaki et al. |

(Continued)

FOREIGN PATENT DOCUMENTS

| JP | H07-154687 A | 6/1995 |
| JP | 2000-155788 A | 6/2000 |

(Continued)

OTHER PUBLICATIONS

International Search Report issued in PCT/JP2021/001025; dated Apr. 6, 2021.

(Continued)

*Primary Examiner* — Sherrie Hsia
(74) *Attorney, Agent, or Firm* — Studebaker & Brackett PC

(57) ABSTRACT

A screen (70) of a display (7) includes a main screen (71), sub-screens (72) and (73), and an input list screen (74). During an examination using an endoscope (1), a control device (4) displays a plurality of types of information on the examination on the main screen (71) and the sub-screens (72) and (73), respectively. In addition, the control device (4) displays, on the input list screen (74), an option of the information to be displayed in a switching target information region included in the main screen (71) and the sub-screens (72) and (73). Moreover, the control device (4) switches the information to be displayed in the switching target information region based on a user operation of selecting the option.

23 Claims, 8 Drawing Sheets

(56) References Cited

U.S. PATENT DOCUMENTS

| | | | |
|---|---|---|---|
| 2015/0272429 A1* | 10/2015 | Shigeta | ............... A61B 1/0002 348/65 |
| 2016/0292498 A1 | 10/2016 | Miura | |
| 2019/0073768 A1 | 3/2019 | Shigeta | |
| 2019/0339836 A1 | 11/2019 | Kanda | |
| 2021/0076917 A1 | 3/2021 | Kamon | |

FOREIGN PATENT DOCUMENTS

| | | | |
|---|---|---|---|
| JP | 2002-032068 A | 1/2002 |
| JP | 2002-272679 A | 9/2002 |
| JP | 2005-110878 A | 4/2005 |
| JP | 2005-279097 A | 10/2005 |
| JP | 2009-219547 A | 10/2009 |
| JP | 2012-081087 A | 4/2012 |
| JP | 2012-085122 A | 4/2012 |
| JP | 2013-153991 A | 8/2013 |
| JP | 2016-189812 A | 11/2016 |
| JP | 2018-112716 A | 7/2018 |
| JP | 2019-042156 A | 3/2019 |
| WO | 2012/008299 A1 | 1/2012 |
| WO | 2018/096987 A1 | 5/2018 |
| WO | 2019/235195 A1 | 12/2019 |

OTHER PUBLICATIONS

International Preliminary Report On Patentability (Chapter I) and Written Opinion of the International Searching Authority issued in PCT/JP2021/001025; dated Sep. 22, 2022.

An Office Action; "Notice of Reasons for Refusal," mailed by the Japanese Patent Office dated Sep. 26, 2023, which corresponds to Japanese Patent Application No. 2022-509301 and is related to U.S. Appl. No. 17/819,837; with English language translation.

An Office Action; "Notice of Reasons for Refusal," mailed by the Japanese Patent Office dated Jan. 9, 2024, which corresponds to Japanese Patent Application No. 2022-509301 and is related to U.S. Appl. No. 17/819,837; with English language translation.

* cited by examiner

ENDOSCOPE SYSTEM, CONTROL METHOD, AND CONTROL PROGRAM

CROSS-REFERENCE TO RELATED APPLICATIONS

This application is a Continuation of PCT International Application No. PCT/JP2021/001025 filed on Jan. 14, 2021, which claims priority under 35 U.S.C § 119(a) to Japanese Patent Application No. 2020-053412 filed on Mar. 24, 2020. Each of the above application(s) is hereby expressly incorporated by reference, in its entirety, into the present application.

BACKGROUND OF THE INVENTION

1. Field of the Invention

The present invention relates to an endoscope system, a control method, and a non-transitory computer readable recording medium storing a control program.

2. Description of the Related Art

In the related art, an endoscope system is known in which continuous imaging is performed while irradiating a subject with normal light, such as white light, to display a live image. In addition, there is known an endoscope system that performs continuous imaging while irradiating a subject with special light, such as narrow band light, and performs analysis such as image-enhanced endoscopy (IEE).

JP2009-219547A discloses a medical image processing device that generates a composite image with an endoscope observation image as a main screen and an endoscope insertion shape image as a sub-screen, or a composite image with an endoscope observation image as a main screen and a captured preview image as a sub-screen.

JP2013-153991A discloses an electronic endoscope system that can set a display mode of a monitor to a single image display mode in which a single image is displayed on the monitor or plural image display mode in which a plurality of images are displayed on the monitor, through an operation of a setting button.

SUMMARY OF THE INVENTION

However, in the related art, in a configuration in which a plurality of types of information on an examination, such endoscopy, are simultaneously displayed on a split screen, it is not possible to easily switch the information to be displayed on the split screen.

For example, in the endoscopy, it is required to also display auxiliary information, such as an analysis result by artificial intelligence (AI) based on, for example, a captured image obtained by an imaging element provided in an endoscope while mainly displaying a live image using the captured image obtained by the imaging element provided in the endoscope on a display.

There are a plurality of types of auxiliary information that should be displayed with the live image. Moreover, among the plurality of types of auxiliary information, it is desirable that the information to be displayed together with the live image can be easily switched by a determination of an examiner (for example, a doctor) based on a situation of the endoscopy. However, the means for solving the problems described above is not disclosed in JP2009-219547A and JP2013-153991A.

The present invention has been made in view of the circumstances described above, and is to provide an endoscope system, a control method, and a non-transitory computer readable recording medium storing a control program that can easily switch information to be displayed on a split screen.

An aspect of the present invention relates to an endoscope system comprising a display capable of being visually recognized by an examiner during an examination using an endoscope, and a processor, in which a screen of the display includes a plurality of information regions and a selection region, and, during the examination, the processor displays a plurality of types of information on the examination in the plurality of information regions, respectively, displays an option of the information to be displayed in a switching target information region included in the plurality of information regions, in the selection region, and switches the information to be displayed in the switching target information region based on a user operation of selecting the option.

In addition, another aspect of the present invention relates to a control method of an endoscope system including a display capable of being visually recognized by an examiner during an examination using an endoscope, in which a screen of the display includes a plurality of information regions and a selection region, the method comprising, during the examination, displaying a plurality of types of information on the examination in the plurality of information regions, respectively, displaying an option of the information to be displayed in a switching target information region included in the plurality of information regions, in the selection region, and switching the information to be displayed in the switching target information region based on a user operation of selecting the option.

In addition, still another aspect of the present invention relates to a non-transitory computer readable recording medium storing a control program that controls an endoscope system including a display capable of being visually recognized by an examiner during an examination using an endoscope, in which a screen of the display includes a plurality of information regions and a selection region, the program causing a computer to execute a process comprising, during the examination, displaying a plurality of types of information on the examination in the plurality of information regions, respectively, displaying an option of the information to be displayed in a switching target information region included in the plurality of information regions, in the selection region, and switching the information to be displayed in the switching target information region based on a user operation of selecting the option.

According to the present invention, it is possible to provide the endoscope system, the control method, and the non-transitory computer readable recording medium storing the control program that can easily switch the information to be displayed on the split screen.

DESCRIPTION OF THE PREFERRED EMBODIMENTS

In the following, an embodiment of the present invention will be described with reference to the drawings.

Endoscope Apparatus 100 which is One Embodiment of Present Invention

Figure 1:
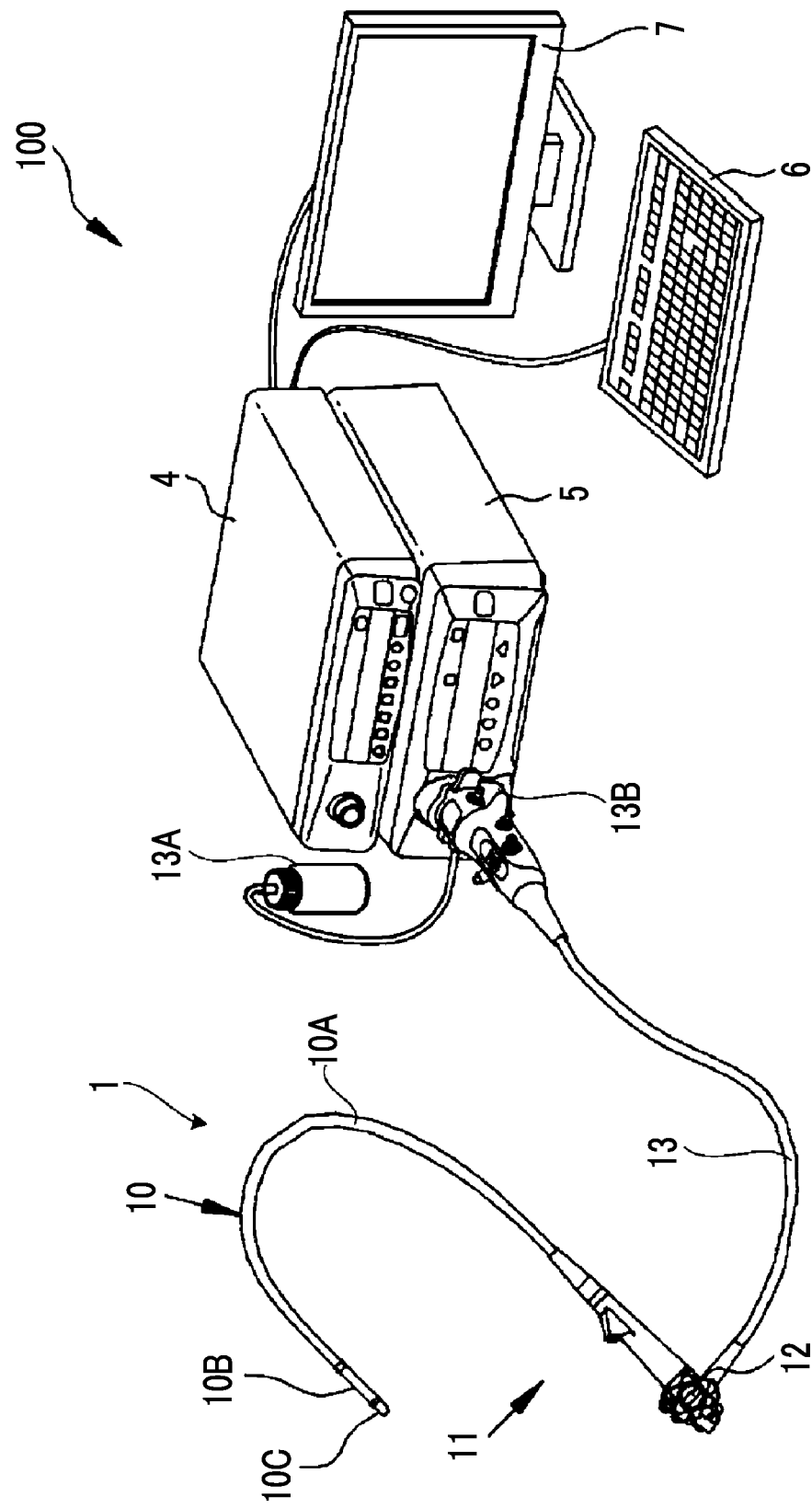
FIG. 1 is a view showing an example of an endoscope apparatus 100 which is one embodiment of the present invention.

FIG. 1 is a view showing an example of an endoscope apparatus 100 which is one embodiment of the present invention.

The endoscope apparatus 100 is an example of an endoscope system according to the embodiment of the present invention. As shown in FIG. 1, the endoscope apparatus 100 comprises an endoscope 1, and a control device 4 and a light source device 5 to which the endoscope 1 is connected. The light source device 5 is an example of a light source capable of switching between a plurality of types of illumination light having different characteristics to perform irradiation.

A display 7 that displays a captured image or the like obtained by imaging an inside of a subject using the endoscope 1 and an input unit 6, which is an interface for inputting various types of information to the control device 4 are connected to the control device 4. The control device 4 controls the endoscope 1, the light source device 5, and the display 7.

The display 7 has a display surface on which display pixels are two-dimensionally arranged, and pixel data constituting image data is drawn on each display pixel on the display surface, thereby performing display of an image based on the image data. The display 7 is an example of a display that can be visually recognized by an examiner (for example, a doctor) during the examination using the endoscope 1.

The endoscope 1 includes an insertion part 10 which is a tubular member extending in one direction and is inserted into the subject, an operating part 11 which is provided in a base end part of the insertion part 10 and includes an operation member for performing an observation mode switching operation, an imaging recording operation, a forcep operation, an air supply/water supply operation, and a suction operation, an angle knob 12 provided adjacent to the operating part 11, and a universal cord 13 including connector portions 13A and 13B that detachably connect the endoscope 1 to the control device 4 and the light source device 5, respectively.

It should be noted that, although not shown in FIG. 1, various channels, such as a forcep hole for inserting forceps for sampling a living body tissue, such as cells or polyps, an air supply/water supply channel, and a suction channel, are provided inside the operating part 11 and the insertion part 10.

The insertion part 10 is composed of a flexible part 10A having flexibility, a bendable part 10B provided at a distal end of the flexible part 10A, and a hard distal end part 10C provided at a distal end of the bendable part 10B.

The bendable part 10B is configured to be bendable by a rotational movement operation of the angle knob 12. Depending on the site of the subject in which the endoscope 1 is used, the bendable part 10B can be bent in any direction and at any angle, and the distal end part 10C can be directed in a desired direction.

<Internal Configuration of Endoscope Apparatus 100 Shown in FIG. 1>

Figure 2:
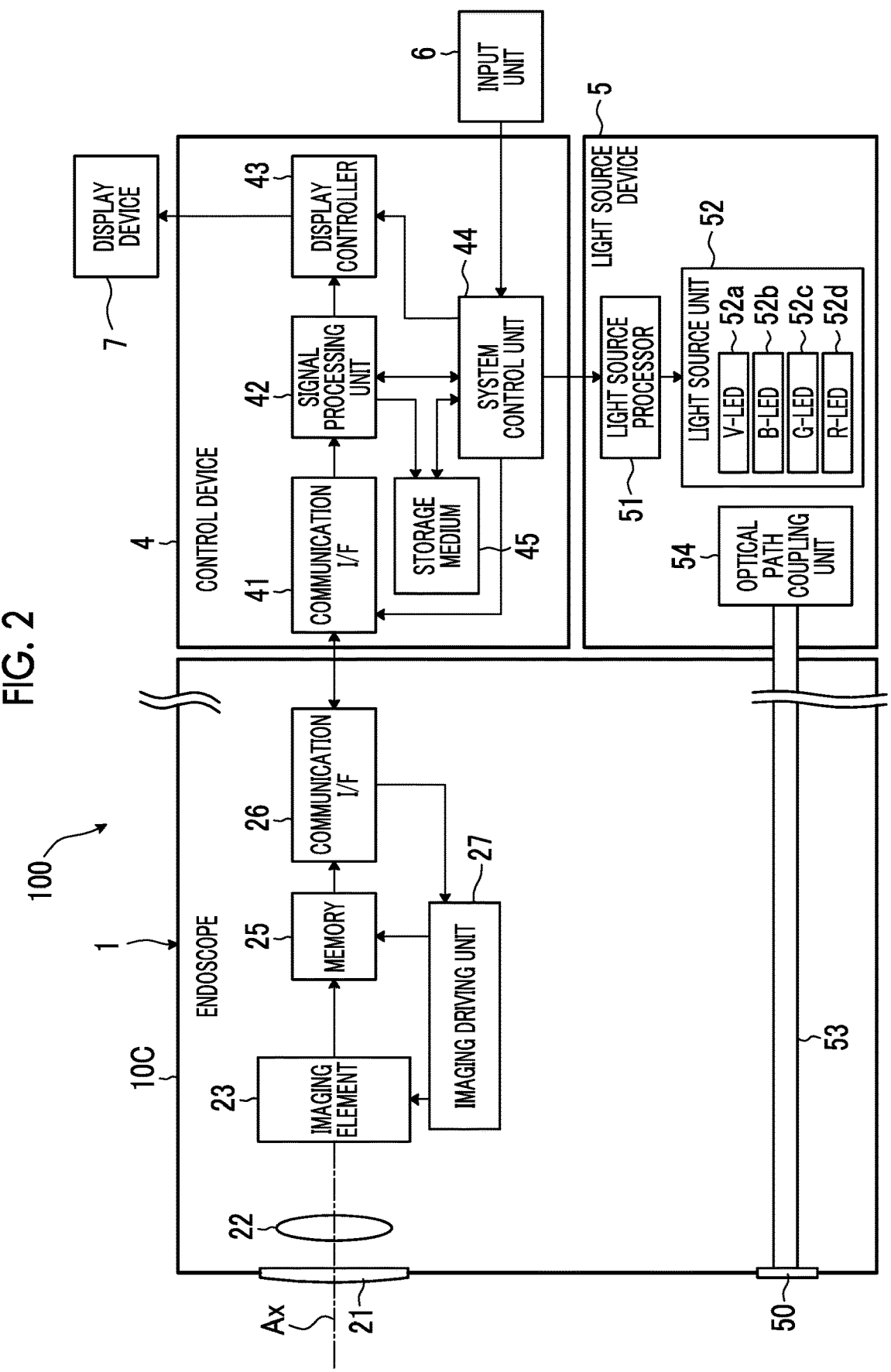
FIG. 2 is a schematic view showing an internal configuration of the endoscope apparatus 100 shown in FIG. 1.
Figure 3:
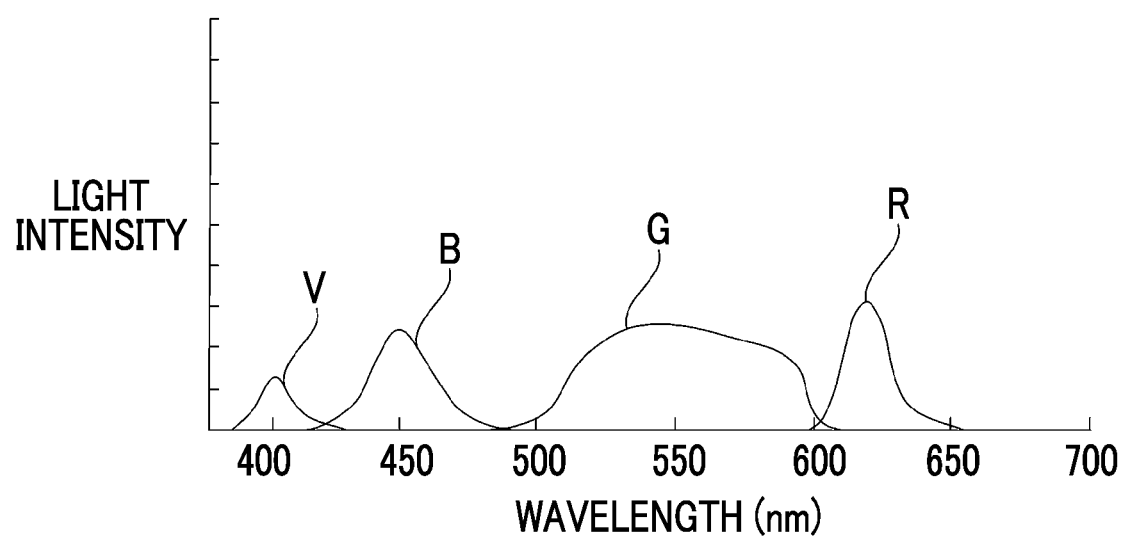
FIG. 3 is a diagram showing an example of a spectrum of light generated by a light source device 5 shown in FIG. 2.

FIG. 2 is a schematic view showing an internal configuration of the endoscope apparatus 100 shown in FIG. 1. FIG. 3 is a diagram showing an example of a spectrum of light generated by the light source device 5 shown in FIG. 2.

The light source device 5 can switch between normal light and special light as illumination light and perform irradiation. The normal light is light having an emission spectrum suitable for recognition by a human, such as a doctor, such as white light. The special light is light having an emission spectrum suitable for image analysis by a computer, such as IEE, which has a different emission spectrum from the normal light.

Specifically, the light source device 5 comprises a light source processor 51, a light source unit 52, and an optical path coupling unit 54. The light source processor 51 is connected to the system control unit 44 of the control device 4, and controls the light source unit 52 based on the command from the system control unit 44.

The light source unit 52 has, for example, a plurality of semiconductor light sources, each of which is turned on or off, and in a case in which the light source unit 52 is turned on, the emission amount of each semiconductor light source is controlled to emit the illumination light for illuminating an observation target. In the present embodiment, the light source unit 52 has LEDs of four colors, a violet light emitting diode (V-LED) 52a, a blue light emitting diode (B-LED) 52b, a green light emitting diode (G-LED) 52c, and a red light emitting diode (R-LED) 52d.

By independently controlling each of the V-LED 52a, the B-LED 52b, the G-LED 52c, and the R-LED 52d, the light source processor 51 can emit violet light V, blue light B, green light G, or red light R by independently changing a light amount. As shown in FIG. 3, the V-LED 52a generates the violet light V of which a central wavelength is in a range of 405±10 nm and a wavelength range is in a range of 380 to 420 nm. The B-LED 52b generates the blue light B of which a central wavelength is in a range of 450±10 nm and a wavelength range is in a range of 420 to 500 nm. The G-LED 52c generates the green light G of which a wavelength range is in a range of 480 to 600 nm. The R-LED 52d generates the red light R of which a central wavelength is in a range of 620 to 630 nm and a wavelength range is in a range of 600 to 650 nm.

In addition, in a case of irradiation with the normal light, the light source processor 51 controls each of the LEDs 52a to 52d to emit the white light in which a light amount ratio of the violet light V, the blue light B, the green light G, and the red light R is Vc:Bc:Gc:Rc. It should be noted that Vc, Bc, Gc, Rc>0.

In addition, in a case of irradiation with the special light, the light source processor 51 controls each of the LEDs 52a to 52d to emit the special light in which the light amount ratio of the violet light V, the blue light B, the green light G, and the red light R as short-wavelength narrow band light is Vs:Bs:Gs:Rs.

The light amount ratio Vs:Bs:Gs:Rs is different from the light amount ratio Vc:Bc:Gc:Rc used in a case of the irradiation with the normal light, and is appropriately determined in accordance with the observation purpose. For example, in a case in which superficial blood vessels are enhanced, it is preferable to make Vs larger than Bs, Gs, and Rs, and in a case in which mesopelagic blood vessels are enhanced, it is preferable to make Gs larger than Vs, Gs, and Rs.

The optical path coupling unit 54 combines each light emitted from the V-LED 52a, the B-LED 52b, the G-LED 52c, and the R-LED 52d, and emits the combined light as the illumination light. The illumination light emitted from the optical path coupling unit 54 of the light source unit 52 enters a light guide 53 to be described below built in the universal cord 13, and is emitted to the subject through an illumination lens 50 provided at the distal end part 10C of the insertion part 10.

In the distal end part 10C of the endoscope 1, an imaging optical system including an objective lens 21 and a lens group 22, an imaging element 23 that images the subject through the imaging optical system, a memory 25, such as a random access memory (RAM), a communication interface (I/F) 26, an imaging driving unit 27, and the light guide 53 for guiding the illumination light emitted from the light source unit 52 to the illumination lens 50 are provided.

The light guide 53 extends from the distal end part 10C to the connector portion 13A of the universal cord 13. The illumination light emitted from the light source unit 52 of the light source device 5 can enter the light guide 53 in a state in which the connector portion 13A of the universal cord 13 is connected to the light source device 5.

A charge coupled device (CCD) image sensor or a complementary metal oxide semiconductor (CMOS) image sensor is used as the imaging element 23. In the present embodiment, the imaging element 23 is the CMOS using a rolling shutter.

The imaging element 23 has a light-receiving surface on which a plurality of pixels are two-dimensionally arranged, and converts an optical image formed on the light-receiving surface by the imaging optical system described above into an electrical signal (imaging signal) in each pixel. Moreover, the imaging element 23 converts the converted imaging signal from an analog signal into a digital signal having a predetermined number of bits, and outputs the imaging signal converted into the digital signal to the memory 25. For example, an imaging element on which a color filter, such as an elementary color or a complementary color, is mounted, is used as the imaging element 23. A set of the imaging signals output from the pixels of the light-receiving surface of the imaging element 23 is referred to as a captured image signal.

The imaging element 23 may be disposed at the distal end part 10C in a state in which the light-receiving surface is perpendicular to an optical axis Ax of the objective lens 21, or may be disposed at the distal end part 10C in a state in which the light-receiving surface is parallel to the optical axis Ax of the objective lens 21.

The imaging optical system provided in the endoscope 1 is composed of optical members (including the lens group 22 described above), such as a lens and a prism, which are present on an optical path of the light from the subject between the imaging element 23 and the objective lens 21, and the objective lens 21. There is also a case in which the imaging optical system is composed of only the objective lens 21.

The memory 25 transitorily records the digital imaging signal output from the imaging element 23.

The communication I/F 26 is connected to a communication interface (I/F) 41 of the control device 4. The communication I/F 26 transmits the imaging signal recorded in the memory 25 to the control device 4 through a signal line in the universal cord 13.

The imaging driving unit 27 is connected to the system control unit 44 of the control device 4 via the communication I/F 26. The imaging driving unit 27 drives the imaging element 23 and the memory 25 based on the command from the system control unit 44 received by the communication I/F 26.

The control device 4 comprises the communication I/F 41, which is connected to the communication I/F 26 of the endoscope 1 by the universal cord 13, a signal processing unit 42, a display controller 43, the system control unit 44, and a recording medium 45.

The communication I/F 41 receives the imaging signal transmitted from the communication I/F 26 of the endoscope 1 to transmit the imaging signal to the signal processing unit 42.

The signal processing unit 42 has a memory that transitorily records the imaging signal received from the communication I/F 41 built therein, and performs processing (image processing, such as demosaicing processing or gamma correction processing) on the captured image signal that is a set of the imaging signals recorded in the memory to generate captured image information in such a format that recognition processing to be described below or the like can be performed. The captured image information generated by the signal processing unit 42 is recorded on the recording medium 45, such as a hard disk or a flash memory.

The display controller 43 displays a captured image based on the captured image information generated by the signal processing unit 42 on the display 7. A coordinate of each pixel data constituting the captured image information generated by the signal processing unit 42 is managed in association with a coordinate of any of the display pixels constituting the di splay surface of the di splay 7.

The system control unit 44 controls each unit of the control device 4, and transmits the command to the imaging driving unit 27 of the endoscope 1 and the light source processor 51 of the light source device 5, and integrally controls the entire endoscope apparatus 100. For example, the system control unit 44 performs the control of the imaging element 23 via the imaging driving unit 27. In addition, the system control unit 44 performs the control of the light source unit 52 via the light source processor 51.

The system control unit 44, the signal processing unit 42, and the display controller 43 include various processors that execute a program to perform processing, a RAM, and a read only memory (ROM).

Examples of various processors include a central processing unit (CPU), which is a general-purpose processor that executes the program to perform various types of processing, a programmable logic device (PLD), which is a processor of which the circuit configuration can be changed after the manufacture, such as a field programmable gate array (FPGA), and a dedicated electric circuit, which is a processor having the circuit configuration specially designed for executing specific processing, such as an application specific integrated circuit (ASIC).

More specifically, the structure of these various processors is an electric circuit in which circuit elements, such as semiconductor elements, are combined.

The system control unit 44, the signal processing unit 42, and the display controller 43 may be composed of one of the various processors, or may be composed of a combination (for example, a combination of a plurality of FPGAs or a combination of a CPU and an FPGA) of two or more processors of the same type or different types.

<Configuration in which Ultrasound Oscillator is Provided>

In addition to the imaging element 23, the endoscope 1 may comprise an ultrasound oscillator that obtains an ultrasound image in a living body. The ultrasound oscillator is an oscillator which oscillates an ultrasound wave and emits the oscillated ultrasound wave. In addition, the ultrasound oscillator is also operated as an ultrasound transducer which receives an echo signal of the emitted ultrasound wave and outputs the received echo signal. The ultrasound image can be obtained by performing various types of image processing on the echo signal output from the ultrasound oscillator, for example, by the processor of the control device 4.

<Schematic Configuration of Imaging Element 23 Shown in FIG. 2>

Figure 4:
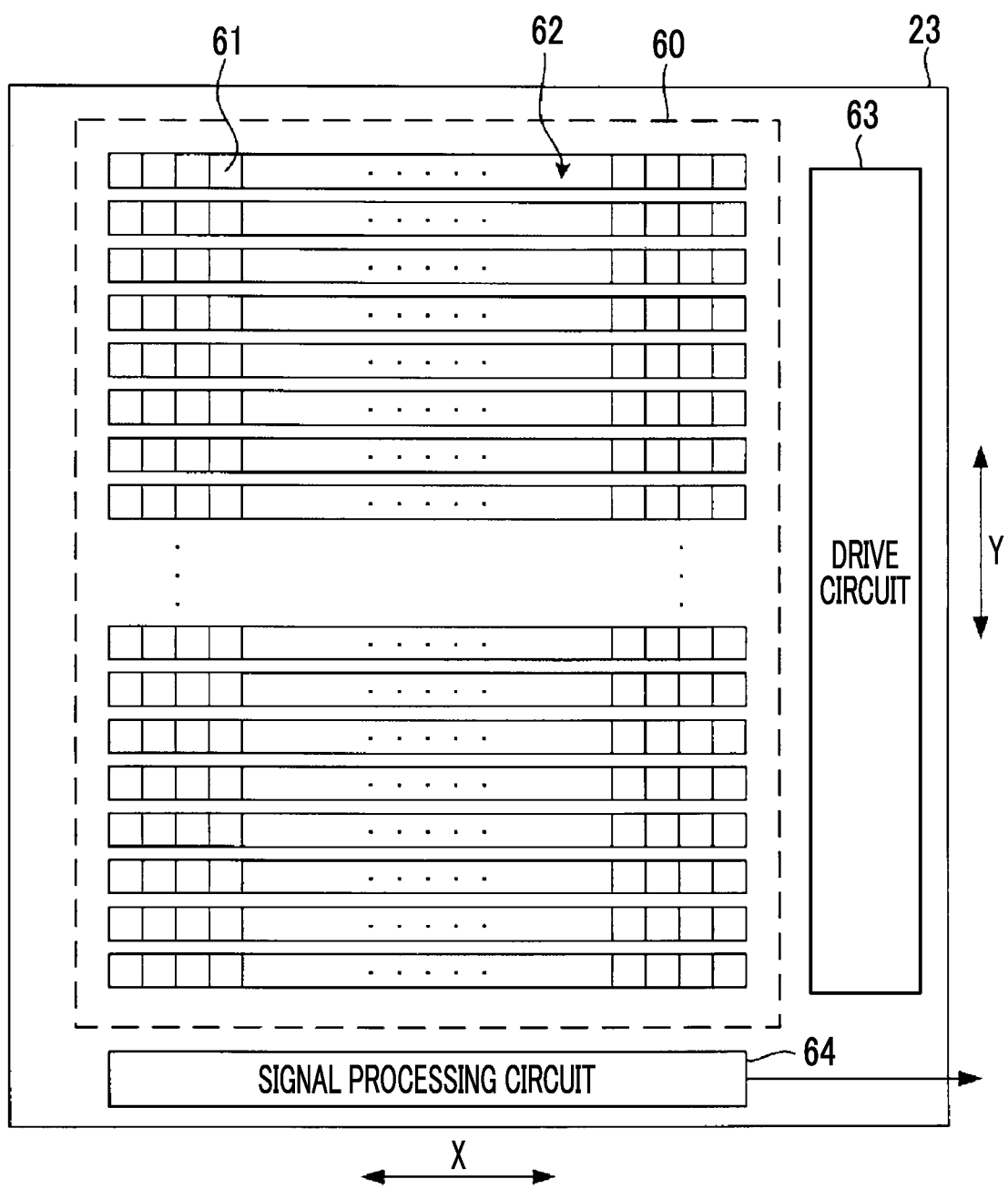
FIG. 4 is a schematic plan view showing a schematic configuration of an imaging element 23 shown in FIG. 2.

FIG. 4 is a schematic plan view showing a schematic configuration of the imaging element 23 shown in FIG. 2.

The imaging element 23 comprises an imaging surface 60 on which a plurality of pixel rows 62 consisting of a plurality of pixels 61 arranged in a row direction X are arranged in a column direction Y orthogonal to the row direction X, a drive circuit 63 that drives the pixels 61 arranged on the imaging surface 60, and a signal processing circuit 64 that processes the pixel signal read out from each pixel 61 of the pixel row 62 arranged on the imaging surface 60 into the signal line. The imaging surface 60 constitutes the light-receiving surface.

In the following, in FIG. 4, an end portion of the imaging surface 60 on one end side (upper side in FIG. 4) in the column direction Y is referred to as an upper end, and an end portion of the imaging surface 60 on the other end side (lower side in FIG. 4) in the column direction Y is referred to as a lower end.

The drive circuit 63 shown in FIG. 4 independently drives each pixel row 62 based on the signal from the imaging driving unit 27, and performs the reset of each pixel 61 included in the pixel row 62 (discharge of charge accumulated in the photoelectric conversion element), the reading out of the pixel signal in accordance with the charge accumulated in the photoelectric conversion element of each pixel 61 into the signal line, and the like.

The signal processing circuit 64 shown in FIG. 4 performs sampling two correlation pile processing on the pixel signal read out from each pixel 61 of the pixel row 62 into the signal line, converts the pixel signal subjected to the sampling two correlation pile processing into the digital signal, and outputs the converted pixel signal. The signal processing circuit 64 is controlled by the imaging driving unit 27.

The signal processing unit 42 performs the signal processing, such as the demosaicing processing and the gamma correction processing, on the pixel signal output from the imaging element 23 to generate the captured image information.

The endoscope apparatus 100 is equipped with a continuous imaging mode that continuously generates a plurality of pieces of the captured image information in accordance with one imaging instruction. In the continuous imaging mode, the system control unit 44 drives the imaging element 23 by the imaging driving unit 27 by a rolling shutter system to image the subject.

The driving of the rolling shutter system includes the rolling reset driving and the rolling read-out driving. The rolling reset driving is driving in which processing of resetting each pixel 61 of the pixel row 62 and starting the exposure of each pixel 61 is sequentially performed while changing the pixel row 62. The rolling read-out driving is driving in which processing of reading out the signal from each pixel 61 of the exposed pixel row 62 and terminating the exposure of the pixel row 62 is sequentially performed while changing the pixel row 62.

<Functional Blocks of Signal Processing Unit 42 Shown in FIG. 2>

Figure 5:
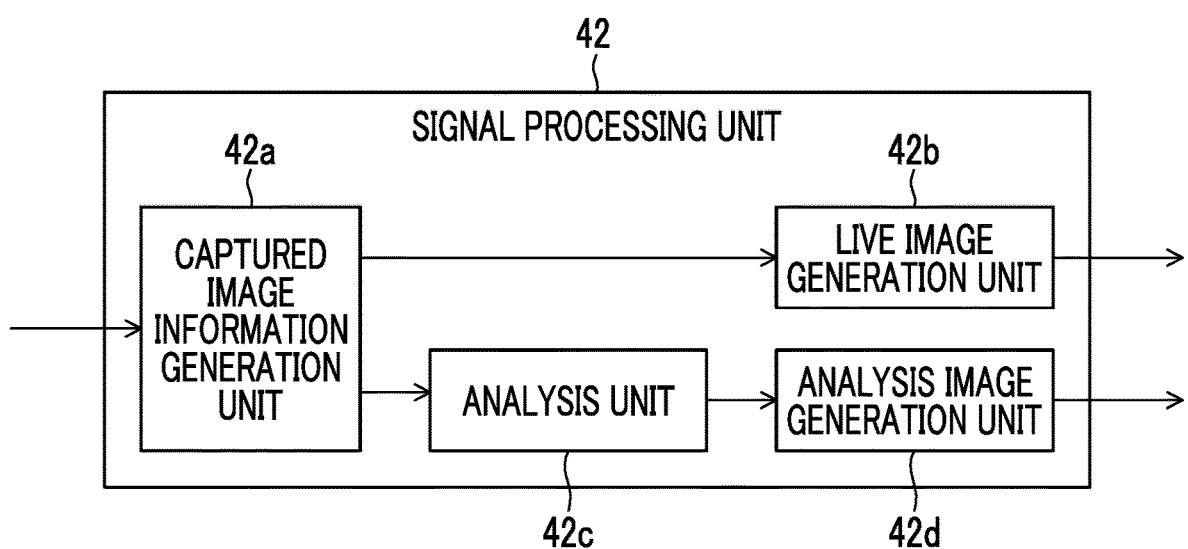
FIG. 5 is a diagram showing an example of functional blocks of a signal processing unit 42 shown in FIG. 2.

FIG. 5 is a diagram showing an example of functional blocks of the signal processing unit 42 shown in FIG. 2.

A processor of the signal processing unit 42, for example, executes a control program stored in the ROM built in the signal processing unit 42 to function as the control device comprising a captured image information generation unit 42a, a live image generation unit 42b, an analysis unit 42c, and an analysis image generation unit 42d.

The captured image information generation unit 42a generates the captured image information by performing the image processing, such as the demosaicing processing or the gamma correction processing, on the imaging signal obtained by imaging of the imaging element 23. The captured image information generation unit 42a outputs the captured image information based on the imaging signal obtained by imaging during the irradiation with the normal light to the live image generation unit 42b as an imaging frame in the generated captured image information, and outputs the captured image information based on the imaging signal obtained by imaging during the irradiation with the special light to the analysis unit 42c as an imaging frame. The imaging frame is the imaging signal obtained by one imaging.

The live image generation unit 42b generates live image information for displaying the live image based on the imaging frame output from the captured image information generation unit 42a, and outputs the generated live image information to the display controller 43 (see FIG. 2) as the captured image information. The live image is the motion picture that displays a result of continuous imaging by the imaging element 23 in real time.

The analysis unit 42c performs the analysis (image analysis) based on the imaging frame output from the captured image information generation unit 42a, and outputs a result of the analysis to the analysis image generation unit 42d. As an example, the analysis unit 42c performs extraction of a contour of the captured image as the analysis. For example, the analysis unit 42c specifies the contour of a biological structure reflected in the image indicated by the captured image information obtained by imaging during the irradiation with the special light. Examples of the biological structure of a specific target include a superficial blood vessel structure, a middle layer blood vessel structure, or a deep blood vessel structure. The analysis by the analysis unit 42c is performed in parallel with displaying of the live image.

The analysis image generation unit 42d generates IEE image information for displaying an IEE image indicating the result of the analysis output from the analysis unit 42c, and outputs the generated IEE image information to the display controller 43 (see FIG. 2) as the captured image information. The IEE image is an image in which the contour of the structure of the subject is enhanced based on the imaging signal obtained by imaging during the irradiation with the special light, such as a blue laser. In this case, the special light, such as the blue laser, constitutes light for image-enhanced endoscopy. For example, the IEE image is an image in which the superficial blood vessel structure is enhanced, an image in which the middle layer blood vessel structure is enhanced, an image in which the deep blood vessel structure is enhanced, and the like.

It should be noted that the image generated by the analysis image generation unit 42d is not limited to the captured image and the processed image of the captured image, and may be an image indicating the numerical value (number or accuracy) or the text (type of tumor) based on the analysis by the analysis unit 42c.

As described with reference to FIG. 5, the endoscope apparatus 100 comprises the analysis unit 42c that performs the analysis based on the captured image information obtained by imaging in a second period in which the special light is emitted in the captured image information. On the other hand, the endoscope apparatus 100 displays the live image based on the captured image information obtained by imaging in a first period in which the normal light is emitted in the captured image information. As a result, it is possible to perform the analysis based on the special light while performing the motion picture display based on the normal light.

<Switching of Illumination Light in Endoscope Apparatus 100>

Figure 6:
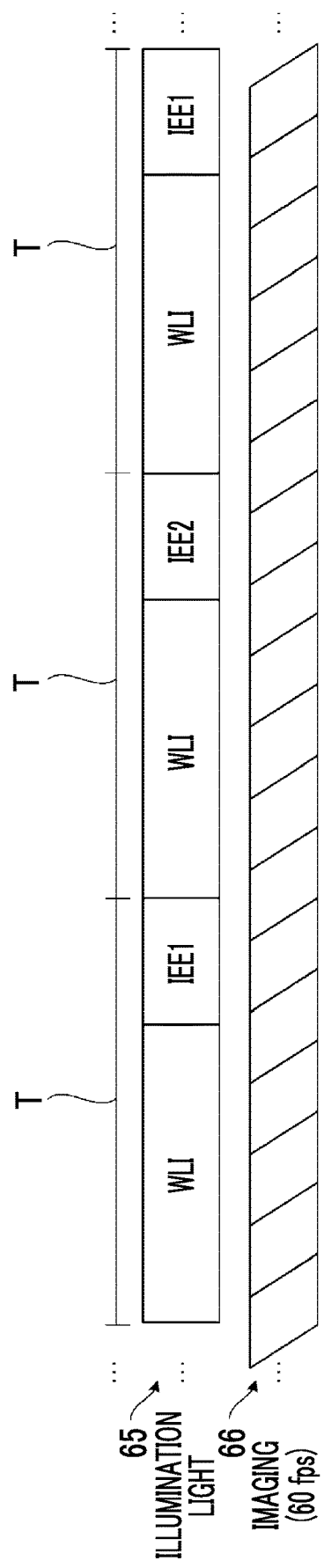
FIG. 6 is a diagram showing an example of switching of illumination light in the endoscope apparatus 100.

FIG. 6 is a diagram showing an example of switching of the illumination light in the endoscope apparatus 100.

An illumination light timing 65 is a timing at which the light source device 5 emits the illumination light in accordance with the command from the control device 4. The WLI in the illumination light timing 65 is a timing at which the light source device 5 emits the normal light, such as the white light, as the illumination light.

The IEE1 in the illumination light timing 65 is a timing at which the light source device 5 emits first special light having a first characteristic, such as narrow band light, as the illumination light. The IEE2 in the illumination light timing 65 is a timing at which the light source device 5 emits second special light having a second characteristic different from the first characteristic as the illumination light.

As shown in the illumination light timing 65, the light source device 5 repeatedly executes a predetermined irradiation operation in a period T. The irradiation operation is an operation of emitting the normal light and then emitting the special light (first special light or second special light). In the example shown in FIG. 6, the light source device 5 alternately switches the special light to be emitted between the first special light and the second special light for each period T. It should be noted that the light source device 5 may use only the first special light as the special light for each period T.

An imaging timing 66 is a timing at which the imaging element 23 performs imaging (exposure) in accordance with the command from the control device 4. A vertical direction at the imaging timing 66 indicates a position of the pixel row 62 in the column direction Y (see FIG. 4). As described above, since the imaging element 23 in the present embodiment performs imaging of the rolling shutter system, the imaging timing 66 deviates for each pixel row 62. In the example shown in FIG. 6, the imaging element 23 performs imaging at a frame rate of 60 frames per second (fps).

As shown in the illumination light timing 65 and the imaging timing 66, the first period in which the light source device 5 continuously emits the normal light extends over a plurality of consecutive frames in imaging by the imaging element 23. In addition, the second period in which the light source device 5 continuously emits the special light extends over at least one frame in imaging by the imaging element 23. In the example shown in FIG. 6, the second period extends over the plurality of consecutive frames by the imaging element 23.

As described above, the light source device 5 repeats the operation of continuously emitting the normal light (illumination light having a first characteristic) over the plurality of consecutive imaging operation frames, and then emitting the special light (illumination light having a second characteristic). Moreover, as described above, the control device 4 displays the live image (motion picture) on the display 7 based on the captured image obtained during the irradiation with the normal light, and performs the analysis based on the captured image obtained during the irradiation with the special light.

<Screen Displayed on Display 7>

Figure 7:
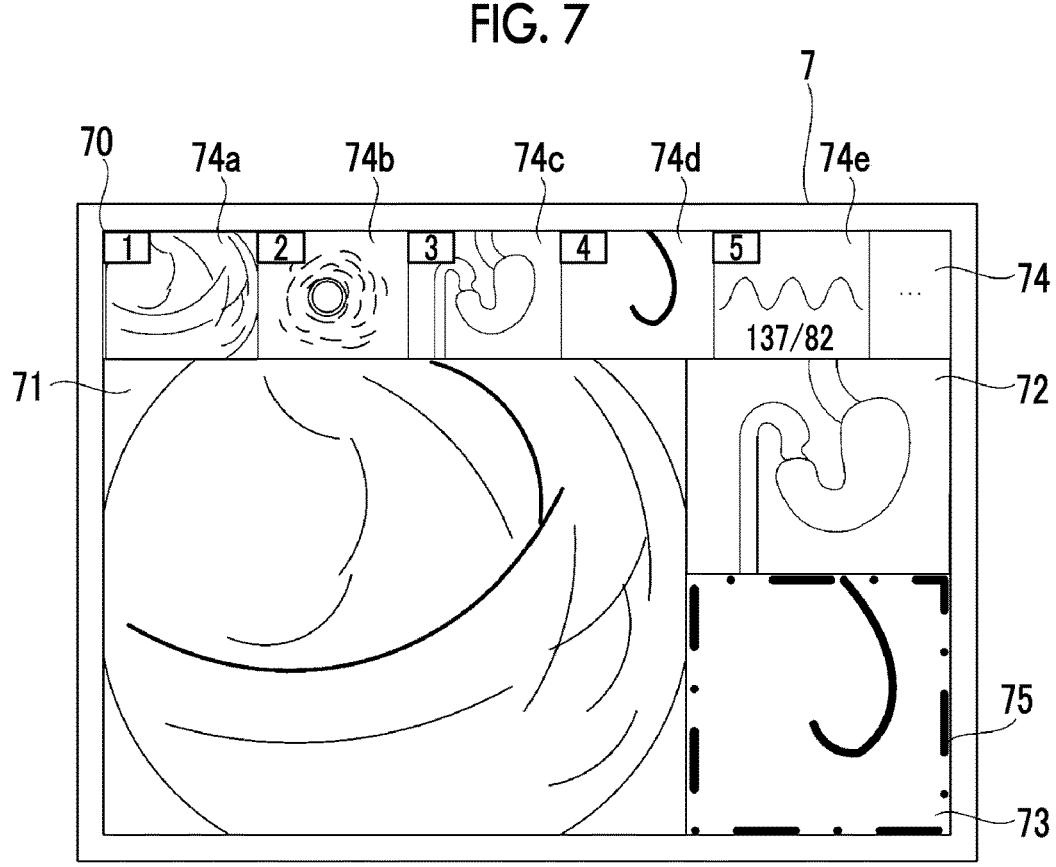
FIG. 7 is a diagram showing an example of a screen displayed on a display 7.
Figure 8:
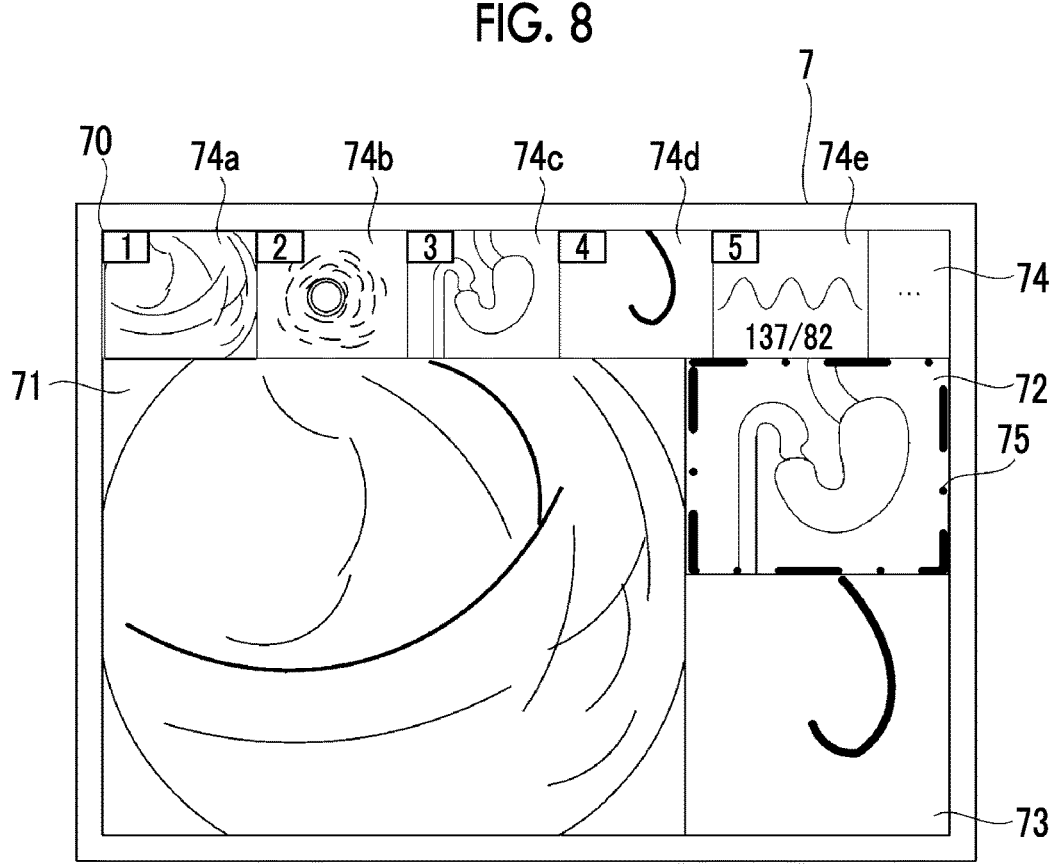
FIG. 8 is a diagram showing an example of changing a switching target information region of displayed information.
Figure 9:
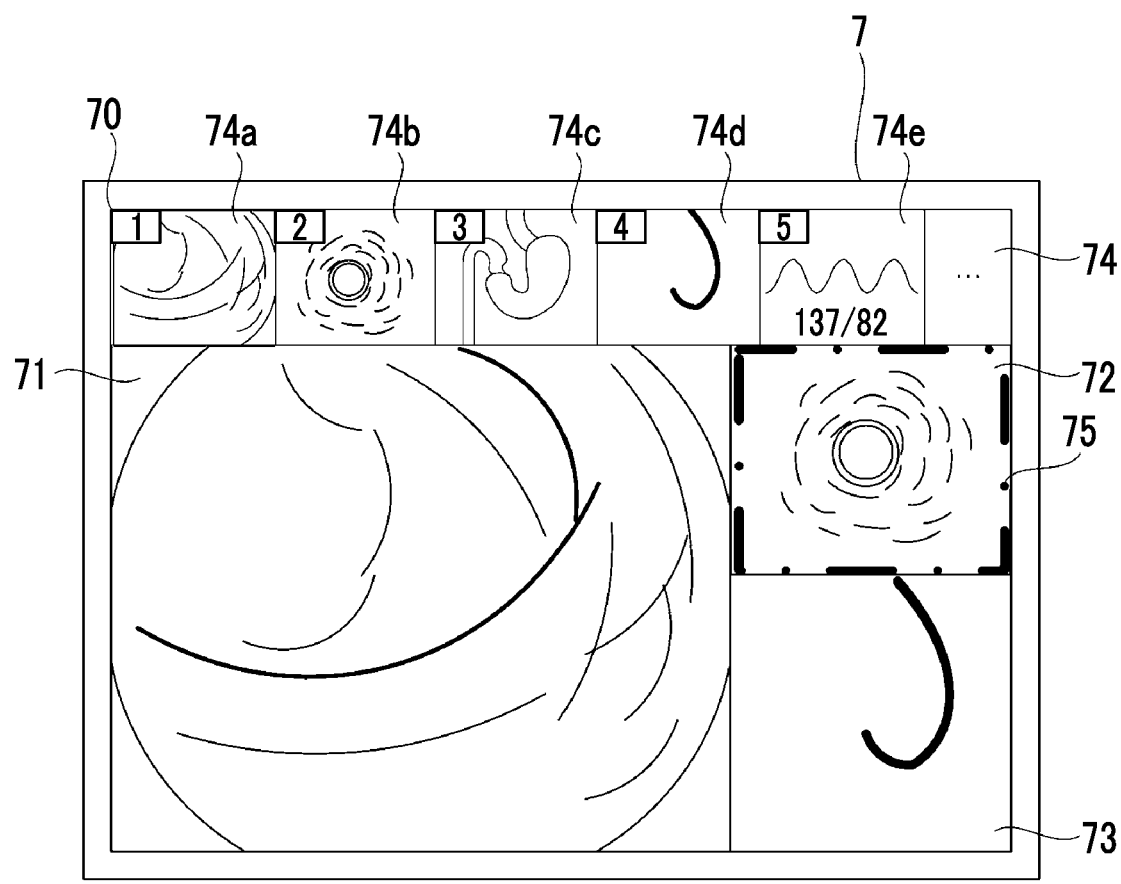
FIG. 9 is a diagram showing an example of switching the displayed information.

FIG. 7 is a diagram showing an example of a screen displayed on the display 7. FIG. 8 is a diagram showing an example of changing a switching target information region of displayed information. FIG. 9 is a diagram showing an example of switching the displayed information.

During the examination using the endoscope 1, the display controller 43 displays, for example, a screen 70 shown in FIG. 7 on the display 7 based on the captured image information output from the signal processing unit 42. The screen 70 includes a main screen 71, sub-screens 72 and 73, and an input list screen 74. The main screen 71 and the sub-screens 72 and 73 are examples of a plurality of information regions according to the embodiment of the present invention. The input list screen 74 is an example of a selection region according to the embodiment of the present invention.

The main screen 71, the sub-screens 72 and 73, and the input list screen 74 are, for example, four split screens divided in terms of software under the control of the control device 4 on one screen of the display 7. It should be noted that the screen 70 may be divided into four, the main screen 71, the sub-screens 72 and 73, and the input list screen 74 in terms of hardware.

The live image based on the live image information output from the live image generation unit 42b of the signal processing unit 42 is displayed on the main screen 71. The information that serves as an auxiliary position for the live image is displayed on the sub-screens 72 and 73. For example, in the example shown in FIG. 7, a stomach map is displayed on the sub-screen 72, and an insertion shape image is displayed on the sub-screen 73.

In this case, the main screen 71 constitutes a first information region in which the motion picture using the captured image obtained from the imaging element 23 provided in the endoscope 1 is displayed. The sub-screens 72 and 73 constitute a second information region in which the information different from the motion picture is displayed.

The stomach map of the sub-screen 72 is an image indicating the stomach of the subject which is the insertion target of the endoscope 1. The stomach map may be, for example, an image obtained by imaging the inside of the subject, or may be a general image of the large intestine prepared in advance.

The insertion shape image of the sub-screen 73 is an image indicating the shape of the insertion part 10 of the endoscope 1 inserted into the stomach inside the subject. For example, the insertion shape image is an image generated based on a detection result of a magnetic field generated from a magnetic field generation element provided in the distal end part 10C of the endoscope 1. In this case, for example, the endoscope apparatus 100 further comprises a magnetic field detection device that detects the magnetic field from the magnetic field generation element of the endoscope 1 inserted into the subject from outside the subject, and the system control unit 44 generates the insertion shape image based on the detection result by the magnetic field detection device.

In addition, the insertion shape image may be an image generated based on the detection result of the magnetic field by the magnetic field detection element provided in the distal end part 10C of the endoscope 1. In this case, for example, the endoscope apparatus 100 further comprises a magnetic field generation element that generates the magnetic field from outside the subject to the inside of the subject, and the system control unit 44 generates the insertion shape image based on the detection result of the magnetic field by the magnetic field detection element provided in the endoscope 1.

By looking at the stomach map and the insertion shape image, the operator of the endoscope 1 can easily insert the insertion part 10 of the endoscope 1 into the stomach.

The input list screen 74 is an image indicating a list of options (menus) of the information that can be displayed on each of the main screen 71 and the sub-screens 72 and 73, for example. In the example shown in FIG. 7, the input list screen 74 includes minified pictures 74a to 74e.

The minified pictures 74a to 74e are minified pictures of the live image, the ultrasound image, the stomach map, the insertion shape image, and a biological information image, respectively. The minified picture of a certain image is an image obtained by minifying the image to a smaller size than a case in which the image is displayed on the main screen 71 or the sub-screens 72 and 73. For example, the minified picture 74a is an image indicating the live image in a smaller size (area) than a case in which the live image is displayed on any of the main screen 71, the sub-screen 72, or the sub-screen 73.

The numbers "1" to "5" are attached to the minified pictures 74a to 74e, respectively. These numbers are numbers for giving an indication by, for example, a numeric keypad included in the input unit 6.

In FIG. 7, a one-dot chain line frame 75 surrounding the sub-screen 73 is information indicating the switching target information region (sub-screen 73 shown in FIG. 7) of the displayed information in the main screen 71 and the sub-screens 72 and 73. The one-dot chain line frame 75 can be moved to any information region of the main screen 71 and the sub-screens 72 and 73 by a user operation via a user interface, such as the input unit 6.

For example, each time a specific user operation is performed on the input unit 6, the information region surrounded by the one-dot chain line frame 75 is switched in the order of the main screen 71, the sub-screen 72, the sub-screen 73, the main screen 71, and so on. FIG. 8 shows a state in which the information region surrounded by the one-dot chain line frame 75 is changed from the main screen 71 to the sub-screen 72. In the example shown in FIG. 8, the sub-screen 72 is the switching target of the displayed information.

For example, in the state shown in FIG. 8, in a case in which the examiner designates "2" by the numeric keypad of the input unit 6, as shown in FIG. 9, the information to be displayed on the sub-screen 72 is switched from the stomach map to the ultrasound image corresponding to the minified picture 74b to which the number "2" is attached.

As described above, during the examination using the endoscope 1, the control device 4 displays a plurality of types of information (three types in the example shown in FIG. 7) on the examination in a plurality of information regions (main screen 71 and sub-screens 72 and 73), respectively.

In addition, the control device 4 displays the switching target information region (sub-screen 72 in the state shown in FIG. 8) included in the plurality of information regions, and displays the minified pictures 74a to 74e as the options of the information on the examination on the input list screen 74 (selection region). Moreover, the information to be displayed in the switching target information region (the sub-screen 72 in the state shown in FIG. 8) is switched based on the user operation of selecting the options displayed on the input list screen 74 (designating the number by the numeric keypad of the input unit 6).

As described above, according to the endoscope apparatus 100, in the configuration in which the plurality of types of information on the endoscopy are simultaneously displayed on the split screen, the information to be displayed on the split screen can be easily switched.

For example, in the endoscopy, it is possible to also simultaneously display the option of the auxiliary information that can be displayed on the sub-screens 72 and 73 while mainly displaying the live image using the captured image obtained by the imaging element 23 provided in the endoscope 1 on the main screen 71 of the display 7. Therefore, the auxiliary information to be displayed together with the live image can be easily switched by the determination of the examiner (for example, the doctor) based on a situation of the endoscopy.

In addition, as shown in FIG. 7, the examiner can intuitively grasp the content of the information indicated by the options in a case in which the options of the information that can be displayed on the main screen 71 and the sub-screens 72 and 73, which are displayed on the input list screen 74, are the minified pictures of the information. As a result, it is possible to easily switch the information to be displayed on the split screen.

In addition, the options of the information that can be displayed on the main screen 71 and the sub-screens 72 and 73 include options of the information that are updated as the examination using the endoscope 1 progresses. For example, the live image is the motion picture that displays the result of continuous imaging by the imaging element 23 in real time as described above, and is updated as the examination progresses. In addition, the ultrasound image, the insertion shape image, the biological information image, and the like can also be the information updated as the examination progresses.

The control device 4 may update the display of the options of the information, which is updated as the examination using the endoscope 1 progresses, on the input list screen 74 as the examination using the endoscope 1 progresses. For example, the minified picture 74a displayed on the input list screen 74 may be a small-sized motion picture that displays consecutive captured images by the imaging element 23 in real time. As another example, for example, the minified picture 74b displayed on the input list screen 74 may be a small-sized motion picture that displays consecutive ultrasound images obtained by the ultrasound oscillator in real time. As a result, the examiner can intuitively grasp the content of the information indicated by the options, and can more easily switch the information to be displayed on the split screen.

Further, in a case in which the control device 4 displays the information updated as the examination using the endoscope 1 progresses on any of the main screen 71, the sub-screen 72, or the sub-screen 73, the control device 4 may update the display of the information at a first frequency and may update the display of the options of the information on the input list screen 74 at a second frequency lower than the first frequency.

As an example, in a case in which the live image is displayed on the main screen 71, the control device 4 updates the live image at a display rate of 60 fps. In addition, the control device 4 updates the minified picture 74a of the live image displayed on the input list screen 74 at a display rate of 6 fps, which is a display rate lower than 60 fps. As a result, the examiner can easily grasp that the information indicated by the minified picture 74a is the live image, and an amount of processing required for updating the display of the minified picture 74a can be reduced.

It should be noted that the information included in the input list screen 74 shown in FIG. 7 is an example and can be set optionally. For example, each information included in the input list screen 74 may be a part of the information shown in FIG. 7. In addition, in addition to the information shown in FIG. 7, or instead of the information shown in FIG. 7, other information (for example, the result of analysis by the analysis unit 42c) may be included in the input list screen 74.

In addition, although the configuration has been described in which the options of the information that can be displayed are the same on the main screen 71 and the sub-screens 72 and 73, a configuration may be adopted in which the options of the information that can be displayed are different on the main screen 71 and the sub-screens 72 and 73. In that case, the control device 4 may display only the information that can be displayed on the input list screen 74 in the information region (switching target information region) surrounded by the one-dot chain line frame 75 on the main screen 71 and the sub-screens 72 and 73.

In addition, although the configuration has been described in which the display switching target information region is the information region selected by the user operation on the main screen 71 and the sub-screens 72 and 73, the present invention is not limited to such a configuration. For example, the information to be displayed on the main screen 71 may be fixed to the live image, and the information region that can be selected by the one-dot chain line frame 75 may be only the sub-screens 72 and 73 (second information regions). In this case, for example, by including the result of the analysis by the analysis unit 42c in the options of the information that can be displayed on the sub-screens 72 and 73, the examiner can also see the result of the analysis which is the auxiliary information while referring to the live image.

Alternatively, the display switching target information region may not be selectable by the user. For example, among the main screen 71 and the sub-screens 72 and 73, only the sub-screen 73 may be the display switching target information region. In this case, the one-dot chain line frame 75 is fixedly displayed on the sub-screen 73 or is not displayed on the screen 70.

In addition, the one-dot chain line frame 75 is an example of information for identifying the switching target information region on the main screen 71 and the sub-screens 72 and 73, and the information for identifying the switching target information region is not limited to the one-dot chain line frame 75.

In addition, as an example of the user operation of selecting the options displayed on the input list screen 74, the designation of the number by the numeric keypad of the input unit 6 has been described, but the present invention is not limited to this. For example, the input unit 6 may include a pointing device, such as a mouse, and the user operation of selecting the options displayed on the input list screen 74 may be the indication (click or the like) of any of the minified pictures 74a to 74e by the pointing device. Alternatively, the display 7 may be a touch panel capable of a touch operation, and the user operation of selecting the options displayed on the input list screen 74 may be the touch of any of the minified pictures 74a to 74e by the touch panel.

Another Example of Analysis

Although the extraction of the contour of the captured image has been described as the analysis by the analysis unit 42c (signal processing unit 42) based on the captured image information obtained by imaging during the irradiation with the special light, the analysis by the analysis unit 42c is not limited to this.

For example, the analysis unit 42c may analyze an insertion shape of the endoscope 1 as the analysis described above. Specifically, the analysis of the insertion shape of the endoscope 1 is specifying of the insertion shape of the insertion part 10 of the endoscope 1 inserted into the subject. For example, the analysis unit 42c specifies the insertion shape of the endoscope 1 based on the change in the captured image information obtained by imaging during the irradiation with the special light. The analysis image generation unit 42d generates image information for displaying an image indicating the insertion shape of the endoscope 1 specified by the analysis unit 42c. As a result, the image indicating the insertion shape of the endoscope 1 is displayed on the sub-screen 72, so that the operator of the endoscope 1 can easily insert the insertion part 10 of the endoscope 1 into the subject.

Alternatively, the analysis unit 42c may detect a region-of-interest inside the subject into which the endoscope 1 is inserted as the analysis described above. For example, the analysis unit 42c detects the region-of-interest inside the subject from the image indicated by the captured image information obtained by imaging during the irradiation with the special light. The region-of-interest is a region that is recommended for attention in the observation of the inside of the subject, such as a region that is likely to be a lesion. The analysis image generation unit 42d generates image information for displaying a region-of-interest-enhanced image in which the region-of-interest detected by the analysis unit 42c is enhanced in the image indicated by the captured image information obtained by imaging during the irradiation with the special light. As a result, the region-of-interest-enhanced image is displayed on a sub-screen 72, and the operator of the endoscope 1 can easily recognize the region-of-interest inside the subject. Alternatively, the analysis image generation unit 42d may generate image information for displaying color difference-expanded image subjected to color difference expansion processing of expanding a color difference between an abnormal site (lesion site), which is the region-of-interest, and a normal site in the image indicated by the captured image information obtained by imaging during the irradiation with the special light. As a result, the color difference-expanded image is displayed on the sub-screen 72, and the operator of the endoscope 1 can easily distinguish between the abnormal site and the normal site inside the subject.

Alternatively, the analysis unit 42c may select a similar case image as the analysis described above. For example, the analysis unit 42c selects a case image similar to the captured image information obtained by imaging during the irradiation with the special light by searching a database accessible to the endoscope apparatus 100. The analysis image generation unit 42d generates image information for displaying an image indicating a selection result by the analysis unit 42c. The selection result by the analysis unit 42c may be the case image itself selected by the analysis unit 42c, or may be information, such as diagnosis result, relating to the case image associated with the case image selected by the analysis unit 42c in the database. As a result, the selection result of the similar case image is displayed on the sub-screen 72, and the operator of the endoscope 1 can easily compare a state inside the subject under observation with the similar case.

Alternatively, the analysis unit 42c may perform determination of a tumor and a non-tumor as the analysis described above. For example, the analysis unit 42c determines whether or not a biological region reflected in the image indicated by the captured image information obtained by imaging during the irradiation with the special light is the tumor. The analysis image generation unit 42d generates image information for displaying an image indicating a determination result by the analysis unit 42c. The determination result by the analysis unit 42c may be information indicating whether or not the biological region reflected in the most recently captured image is the tumor, or may be information indicating the number of the biological regions determined to be the tumor from the start of the current examination. As a result, the determination result of the tumor and the non-tumor is displayed on the sub-screen 72, and it is possible to support the observation or the operation of the endoscope 1 by the operator of the endoscope 1.

Alternatively, the analysis unit 42c may specify a state of an organ as the analysis described above. For example, the analysis unit 42c specifies the state of the organ reflected in the image indicated by the captured image information obtained by imaging during the irradiation with the special light. Examples of the state of the organ include the oxygen saturation for each region, the thickness, the density, pattern, and the uniformity of the blood vessel structure, the surface structure of the large intestine (for example, pit pattern structure), or the surface structure of the duodenum (for example, villous structure). The analysis image generation unit 42d generates image information for displaying an image indicating a specifying result by the analysis unit 42c. For example, the analysis image generation unit 42d generates an oxygen saturation image obtained by imaging the oxygen saturation for each specified region. As a result, the specifying result of the state of the organ is displayed on the sub-screen 72, and it is possible to support the observation or the operation of the endoscope 1 by the operator of the endoscope 1.

Alternatively, the analysis unit 42c may generate a planned separation line as the analysis described above. For example, the analysis unit 42c decides the planned separation line (demarcation line) which is the line to be separated to remove the tumor in the biological region reflected in the image indicated by the captured image information obtained by imaging during the irradiation with the special light. The analysis image generation unit 42d generates image information for displaying an image to which the planned separation line decided by the analysis unit 42c is attached in the image indicated by the captured image information obtained by imaging during the irradiation with the special light. As a result, the image to which the planned separation line is attached is displayed on the sub-screen 72, and the operator of the endoscope 1 can easily recognize the planned separation line inside the subject.

Modification Examples of First Period, Second Period, and Period T

Although the configuration has been described in which the length of each of the first period in which the normal light is emitted and the second period in which the special light is emitted is fixed in the repetition for each period T, but the length of each of the first period in which the normal light is emitted and the second period in which the special light is emitted does not have to be fixed (may be variable) in the repetition for each period T. For example, a ratio of the lengths of the first period and the second period in one period T may be 3:1, and a ratio of the lengths of the first period and the second period in the other period T may be 3:2.

In addition, although the case has been described in which the period T, which is the repetition period of the operation of emitting the normal light and the special light, is fixed, the period T may be variable. In addition, the configuration has been described in which the normal light is first emitted and then the special light is emitted in the period T, a configuration may be adopted in which the special light is first emitted and then the normal light is emitted in the period T.

In addition, the spectrum of the normal light may be fixed in the repetition for each period T or may be variable in the repetition for each period T. Similarly, the spectrum of the special light may be fixed in the repetition for each period T or may be variable in the repetition for each period T.

In addition, although the configuration has been described in which the second period in which the special light is emitted is immediately after the first period in which the normal light is emitted, a non-irradiation period in which the light source device 5 does not emit the illumination light may be present between the first period and the second period.

In addition, a configuration may be adopted in which narrow band short wavelength dimming light and white light are simultaneously emitted as the normal light or the special light described above. As a result, minute differences in color are enhanced and displayed, and the observation, such as inflammation observation or pick-up observation, is facilitated.

Another Example of Imaging Element 23

Although the configuration has been described in which the imaging element 23 having the rolling shutter system is used, a configuration may be adopted in which the imaging element 23 having the global shutter system is used.

Another Embodiment of Endoscope System

The endoscope apparatus 100 has been described as an example of the endoscope system according to the embodiment of the present invention, the endoscope system according to the embodiment of the present invention may be realized by a plurality of devices connected to each other via the network. For example, a configuration may be adopted in which at least a part of the processing by the control device 4 described above is executed by another device connected to the endoscope apparatus 100 via the network.

(Control Program)

A control program, which is stored in the ROM of the control device 4, is stored in a program computer-readable non-transitory storage medium. Examples of such a "computer-readable storage medium" include an optical medium, such as a compact disc-ROM (CD-ROM), and a magnetic storage medium, such as a universal serial bus (USB) memory, or a memory card. Such a program can be provided by being downloaded via a network.

As described above, in the present specification, the following matters are disclosed.

(1)

An endoscope system comprising a display capable of being visually recognized by an examiner during an examination using an endoscope, and a processor, in which a screen of the display includes a plurality of information regions and a selection region, and, during the examination, the processor displays a plurality of types of information on the examination in the plurality of information regions, respectively, displays an option of the information to be displayed in a switching target information region included in the plurality of information regions, in the selection region, and switches the information to be displayed in the switching target information region based on a user operation of selecting the option.

(2)

The endoscope system according to (1), in which the switching target information region is an information region selected by the user operation from among the plurality of information regions.

(3)

The endoscope system according to (1) or (2), in which the option of the information is an image including a minified picture of the information.

(4)

The endoscope system according to any one of (1) to (3), in which the option of the information includes an option of information updated as the examination progresses.

(5)

The endoscope system according to (4), in which the processor updates display of the option of the information, which is updated as the examination progresses, in the selection region as the examination progresses.

(6)

The endoscope system according to (4) or (5), in which the processor updates display of the information at a first frequency in a case in which the information updated as the examination progresses is displayed in the information region, and updates display of the option of the information, which is updated as the examination progresses, in the selection region at a second frequency lower than the first frequency.

(7)

The endoscope system according to any one of (1) to (6), in which the plurality of information regions include a first information region in which a motion picture using a captured image obtained from an imaging element provided in the endoscope is displayed, and a second information region in which information different from the motion picture is displayed, and the switching target information region is included in the second information region.

(8)

The endoscope system according to (7), in which, in the second information region, the plurality of types of information on the examination including a result of analysis based on the captured image are switchable and displayable, and, in the selection region, the plurality of types of information on the examination including the result of the analysis are displayed as the option.

(9)

The endoscope system according to (8), further comprising a light source capable of switching between a plurality of types of illumination light having different characteristics to perform irradiation, in which the light source repeats an operation of continuously emitting illumination light having a first characteristic in a first period over a plurality of consecutive imaging operation frames, and then emitting illumination light having a second characteristic different from the first characteristic in a second period over at least one imaging operation frame, and the processor performs the analysis based on the captured image obtained in the second period.

(10)

The endoscope system according to (9), in which the illumination light having the first characteristic is white light, and the illumination light having the second characteristic is light for image-enhanced endoscopy.

(11)

The endoscope system according to (9) or (10), in which a length of each of the first period and the second period is fixed in repetition of the operation or is variable in repetition of the operation.

(12)

The endoscope system according to any one of (9) to (11), in which spectra of the illumination light having the first characteristic and the illumination light having the second characteristic are fixed in repetition of the operation or is variable in repetition of the operation.

(13)

The endoscope system according to any one of (9) to (12) in which a non-irradiation period of the light source is present between the first period and the second period.

(14)

The endoscope system according to any one of (9) to (13), in which the first period is a period longer than the second period.

(15)

The endoscope system according to any one of (8) to (14), in which the analysis includes analysis of an insertion shape of the endoscope including the imaging element.

(16)

The endoscope system according to any one of (8) to (15), in which the analysis includes extraction of a contour of the captured image.

(17)

The endoscope system according to any one of (8) to (16), in which the analysis includes detection of a region-of-interest inside a subject into which the endoscope including the imaging element is inserted.

(18)

The endoscope system according to any one of (8) to (17), in which the analysis includes selection of a similar case image.

(19)

The endoscope system according to any one of (8) to (18), in which the analysis includes information for supporting determination of a tumor and a non-tumor.

(20)

The endoscope system according to any one of (8) to (19), in which the analysis includes specifying of a state of an organ.

(21)

The endoscope system according to any one of (8) to (20), in which the analysis includes generation of a planned separation line.

(22)

A control method of an endoscope system including a display capable of being visually recognized by an examiner during an examination using an endoscope, in which a screen of the display includes a plurality of information regions and a selection region, the method comprising, during the examination, displaying a plurality of types of information on the examination in the plurality of information regions, respectively, displaying an option of the information to be displayed in a switching target information region included in the plurality of information regions, in the selection region, and switching the information to be displayed in the switching target information region based on a user operation of selecting the option.

(23)

A control program that controls an endoscope system including a display capable of being visually recognized by an examiner during an examination using an endoscope, in which a screen of the display includes a plurality of information regions and a selection region, the program causing a computer to execute a process comprising, during the examination, displaying a plurality of types of information on the examination in the plurality of information regions, respectively, displaying an option of the information to be displayed in a switching target information region included in the plurality of information regions, in the selection region, and switching the information to be displayed in the switching target information region based on a user operation of selecting the option.

According to the present invention, it is possible to provide the endoscope system, the control method, and the control program that can easily switch the information to be displayed on the split screen.

EXPLANATION OF REFERENCES

1: endoscope
4: control device
5: light source device
6: input unit
7: display
10: insertion part
10A: flexible part
10B: bendable part
10C: distal end part
11: operating part
12: angle knob
13: universal cord
13A, 13B: connector portion
21: objective lens
22: lens group
23: imaging element
25: memory
26, 41: communication OF
27: imaging driving unit
42: signal processing unit
42a: captured image information generation unit
42b: live image generation unit
42c: analysis unit
42d: analysis image generation unit
43: display controller
44: system control unit
45: recording medium
50: illumination lens
51: light source processor
52: light source unit
52a: V-LED
52b: B-LED
52c: G-LED
52d: R-LED
53: light guide
54: optical path coupling unit
60: imaging surface
61: pixel
62: pixel row
63: drive circuit
64: signal processing circuit
65: illumination light timing
66: imaging timing
70: screen
71: main screen
72, 73: sub-screen
74: input list screen
74a to 74e: minified picture
75: one-dot chain line frame
100: endoscope apparatus

What is claimed is:

1. An endoscope system comprising:
a display capable of being visually recognized by an examiner during an examination using an endoscope; and
a processor,
wherein a screen of the display includes a plurality of information regions and a selection region, and
during the examination, the processor
displays a plurality of types of information on the examination in the plurality of information regions, respectively,
displays an option of the information to be displayed in a switching target information region included in the plurality of information regions, in the selection region, and
switches the information to be displayed in the switching target information region based on a user operation of selecting the option.

2. The endoscope system according to claim 1, wherein the switching target information region is an information region selected by the user operation from among the plurality of information regions.

3. The endoscope system according to claim 1, wherein the option of the information is an image including a minified picture of the information.

4. The endoscope system according to claim 1, wherein the option of the information includes an option of information updated as the examination progresses.

5. The endoscope system according to claim 4, wherein the processor updates display of the option of the information, which is updated as the examination progresses, in the selection region as the examination progresses.

6. The endoscope system according to claim 4, wherein the processor
updates display of the information at a first frequency in a case in which the information updated as the examination progresses is displayed in the information region, and
updates display of the option of the information, which is updated as the examination progresses, in the selection region at a second frequency lower than the first frequency.

7. The endoscope system according to claim 1, wherein the plurality of information regions include a first information region in which a motion picture using a captured image obtained from an imaging element provided in the endoscope is displayed, and a second information region in which information different from the motion picture is displayed, and
the switching target information region is included in the second information region.

8. The endoscope system according to claim 7,
wherein, in the second information region, the plurality of types of information on the examination including a result of analysis based on the captured image are switchable and displayable, and
in the selection region, the plurality of types of information on the examination including the result of the analysis are displayed as the option.

9. The endoscope system according to claim 8, further comprising:
a light source capable of switching between a plurality of types of illumination light having different characteristics to perform irradiation,
wherein the light source repeats an operation of continuously emitting illumination light having a first characteristic in a first period over a plurality of consecutive imaging operation frames, and then emitting illumination light having a second characteristic different from the first characteristic in a second period over at least one imaging operation frame, and
the processor performs the analysis based on the captured image obtained in the second period.

10. The endoscope system according to claim 9,
wherein the illumination light having the first characteristic is white light, and
the illumination light having the second characteristic is light for image-enhanced endoscopy.

11. The endoscope system according to claim 9,
wherein a length of each of the first period and the second period is fixed in repetition of the operation or is variable in repetition of the operation.

12. The endoscope system according to claim 9,
wherein spectra of the illumination light having the first characteristic and the illumination light having the second characteristic are fixed in repetition of the operation or is variable in repetition of the operation.

13. The endoscope system according to claim 9,
wherein a non-irradiation period of the light source is present between the first period and the second period.

14. The endoscope system according to claim 9,
wherein the first period is a period longer than the second period.

15. The endoscope system according to claim 8,
wherein the analysis includes analysis of an insertion shape of the endoscope including the imaging element.

16. The endoscope system according to claim 8,
wherein the analysis includes extraction of a contour of the captured image.

17. The endoscope system according to claim 8,
wherein the analysis includes detection of a region-of-interest inside a subject into which the endoscope including the imaging element is inserted.

18. The endoscope system according to claim 8,
wherein the analysis includes selection of a similar case image.

19. The endoscope system according to claim 8,
wherein the analysis includes information for supporting determination of a tumor and a non-tumor.

20. The endoscope system according to claim 8,
wherein the analysis includes specifying of a state of an organ.

21. The endoscope system according to claim 8,
wherein the analysis includes generation of a planned separation line.

22. A control method of an endoscope system including a display capable of being visually recognized by an examiner during an examination using an endoscope, in which a screen of the display includes a plurality of information regions and a selection region, the method comprising:
during the examination,
displaying a plurality of types of information on the examination in the plurality of information regions, respectively;
displaying an option of the information to be displayed in a switching target information region included in the plurality of information regions, in the selection region; and
switching the information to be displayed in the switching target information region based on a user operation of selecting the option.

23. A non-transitory computer readable recording medium storing a control program that controls an endoscope system including a display capable of being visually recognized by an examiner during an examination using an endoscope, in which a screen of the display includes a plurality of information regions and a selection region, the program causing a computer to execute a process comprising:
during the examination,
displaying a plurality of types of information on the examination in the plurality of information regions, respectively;
displaying an option of the information to be displayed in a switching target information region included in the plurality of information regions, in the selection region; and
switching the information to be displayed in the switching target information region based on a user operation of selecting the option.

* * * * *